United States Patent [19]

Johnson et al.

[11] 4,048,190
[45] Sept. 13, 1977

[54] PREPARATION OF BISPHENOL-A BISIMIDES

[75] Inventors: Donald S. Johnson; Frank J. Williams, III, both of Scotia, N.Y.

[73] Assignee: General Electric Company, Schenectady, N.Y.

[21] Appl. No.: 658,501

[22] Filed: Feb. 17, 1976

[51] Int. Cl.² .......................................... C07D 209/34
[52] U.S. Cl. .......................... 260/326 N; 260/47 CP; 260/326 A; 260/346.3
[58] Field of Search .................................... 260/326 N

[56] References Cited

U.S. PATENT DOCUMENTS

| | | | |
|---|---|---|---|
| 3,879,428 | 4/1975 | Heath et al. | 260/326 N |
| 3,923,828 | 12/1975 | Williams | 260/326 N |
| 3,992,407 | 11/1976 | Markezich | 260/326 N |

OTHER PUBLICATIONS

Craig et al., "Technique of Org. Chem.," vol. III, pp. 296–297 (1950).
Cheronis et al., "Semimicro Qual. Org. Anal.," 2nd Ed., pp. 33–37 (1958).

*Primary Examiner*—Ethel G. Love
*Attorney, Agent, or Firm*—Joseph T. Cohen; Jerome C. Squillaro

[57] ABSTRACT

A process for purifying a bisphenol-A bisimide which comprises treating the latter with a polar solvent selected from the class consisting of methanol, acetonitrile, acetone, and diethyl ether.

1 Claim, No Drawings

PREPARATION OF BISPHENOL-A BISIMIDES

This invention is concerned with the preparation of a bisphenol-A bisimide, specifically 2,2-bis[4(3,4-dicarboxyphenoxy)phenyl]propane-bis-N-methylphthalimide (hereinafter referred to as BPA-BI). The latter BPA-BI has been used to make a bisphenol A-dianhydride (hereinafter identified as BPA-DA) corresponding to the formula

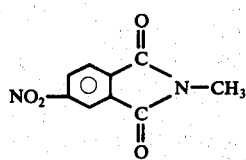

It has been found that the purity of the BPA-BI has an important influence on the quality and properties of the heat-resistant polyimide resins obtained from the reaction of the BPA-dianhydride (made from the precursor BPA-BI) and an organic diamine of the formula $NH_2$—R—$NH_2$ where R is a divalent organic radical of from 1 to 20 carbon atoms, including such diamines as methylene dianiline, m-phenylene diamine, p-phenylene diamine, etc. The preparation of such polyimide resins from the reaction of the BPA-dianhydride and an organic diamine is more fully disclosed and claimed in U.S. Pat. No. 3,847,867 issued Nov. 12, 1974 and assigned to the same assignee as the present invention.

The usual manner for making the BPA-BI involves interacting, in the presence of an alkali-metal hydroxide and a suitable solvent, 4-nitro-N-methylphthalimide of the formula

II

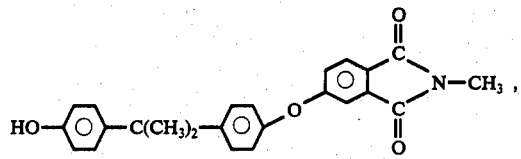

with bisphenol-A of the formula

III

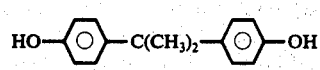

The BPA-BI thus formed can then be hydrolyzed to the tetraacid derivative and dehydrated to give the BPA-dianhydride for use with the organic diamines to make the polyimides. The synthesis of the BPA-BI and its conversion to the dianhydride is more specifically disclosed and claimed in U.S. Pat. No. 3,879,428, issued Apr. 22, 1975 and assigned to the same assignee as the present invention.

Since the thermal stability and other properties of the polyimide resins are very much dependent on the purity of the BPA-dianhydride used, and since it has been found that deriving the BPA-dianhydride from the normally produced BPA-BI has resulted in a purity of the BPA-dianhydride of less than what is desired because of impurities in the BPA-BI, particularly the 3,4-substituted isomer of the BPA-BI of the formula

IV

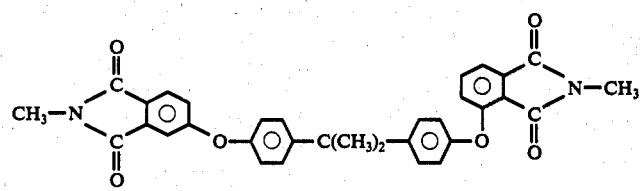

and another impurity of the formula

V

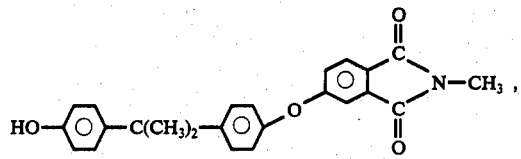

it has been found desirable to reduce the impurities in the BPA-BI which cause the above-described reduction in properties of the polyimide resins. Attempts to eliminate these two impurities from the BPA-BI before conversion to the BPA-dianhydride have generally been either unsuccessful or have required such extensive processing that often the economical isolation of a pure BPA-dianhydride becomes extremely difficult.

Unexpectedly, we have discovered that the crude BPA-BI mixture contaminated with either the 3,4-isomer of formula IV or the monoimide of formula V, or both these materials which often, respectively, on a weight basis, range from 5 to 10% of the former and from 2 to 10% of the latter impurities, based on the total weight of the BPA-BI, can be treated with a selected group of low boiling polar solvents such as methanol, acetone, acetonitrile, and diethyl ether by dissolving the BPA-BI with the impurities in such solvent, or a mixture of these solvents, at temperatures ranging from about 20° C. to 100° C., filtering the resulting heterogeneous mixture, and recovering essentially pure BPA-BI almost completely free of the impurities of formulas IV and V. It was also found that by removing these impurities, the color of the BPA-BI thus obtained was much lighter than was the case before treatment in accordance with the procedure embraced by our invention. In general the recovery of the BPA-BI was usually in yields in excess of 93% of the theoretical yield, with the exception of that when using acetone.

The amount of solvent used with the impure BPA-BI is not critical and can be varied widely and can range on a weight basis, from 1 to as high as 10 or more parts of the solvent per part of the crude BPA-BI. The reaction with the solvent generally is completed in a relatively short period of time ranging from about 15 minutes to two or three hours or more. The temperature at which the removal of the impurities in the specific solvent takes place is not critical and can range from ambient temperatures to as high as 50°-100° C. Generally reflux temperatures of the mixtures can be used when elevated temperatures are employed.

Upon cooling the reaction mixture, it is filtered to remove the solid material. The solid is then washed, advantageously with the same solvent used to remove the impurities, and then dried.

We have found that by using the purified BPA-dianhydride obtained in the course of our process based on the use of the purified BPA-BI, polyimides made from such BPA-dianhydride and meta-phenylene diamine gave resins of excellent thermal stability; that is, they are stable at 300° C. and even after three hours in air, at this temperature less than 1% gel formed. If the unpurified BPA-BI is used initially to make the BPA-dianhydride, then polyimides formed from the same meta-phenylene diamine gave a polyimide which showed 20% gel after heating at 300° C. for three hours in air.

In order that those skilled in the art may better understand how the present invention may be practiced, the following example is given by way of illustration and not by way of limitation. All parts are by weight.

The crude BPA-BI used was the result of reacting the 4-nitro-N-methylphthalimide with bisphenol-A in the manner referred to above in U.S. Pat. No. 3,879,482; this material contained from 5 to 10% of the 3,4-isomer of formula IV and from 2 to 10% of the monoimide of formula V.

EXAMPLE 1

The experimental procedure whereby various tests were conducted in making the BPA-BI, having the formula

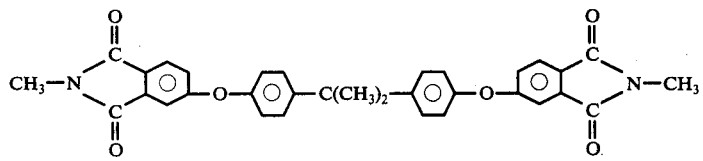

involved using two parts of the crude BPA-BI referred to above and stirring the latter at room temperature or at reflux temperature, as the case may be, with five parts of the respective solvent for a period of about 30 minutes. The mixture of ingredients was cooled to room temperature and filtered. The filtrate was washed with 10 parts of the specific solvent used to give the purified BPA-BI. The melting point of the crude material was within the range of 128°-140° C., while the melting point of the washed purified BPA-BI obtained in this example ranged from about 143°-149° C. The following Table 1 shows the results of a number of runs using various solvents and mixtures of solvents (which are intended to be included in the scope of the claimed invention), together with the conditions of reaction and the present recovery of BPA-BI. The melting point of the recovered BPA-BI is also recited. The purity of the BPA-BI was established by the use of $^{13}C$ NMR. In all instances, no impurity of formula IV was found, and trace impurities (less than 1%) were found only in those tests using solvents other than methanol alone.

TABLE 1.

| Solvent | Conditions | % Recovery of BPA-BI | ° C. M.P. Washed Material | Impurities Established by $^{13}C$ NMR |
|---|---|---|---|---|
| CH$_3$OH | Room Temp. | 99% | 146-148 | None |
| CH$_3$OH | Reflux | 99% | 147-149 | None |
| Acetone | Room Temp. | 93% | 143-146 | Trace formula V |
| Acetone | Reflux | 83% | 145.5-147.5 | Trace formula V |
| CH$_3$OH/ Acetone (50%/50%) | Reflux | 93% | 144-146 | Trace formula V |
| Diethyl Ether | Room Temp. | 96% | 1421-145 | Trace formula V |
| Acetonitrile | Room Temp. | 96% | 146-148 | Trace formula V |

The method of contacting the impure BPA-BI with the particular solvent, e.g., the methanol, can take various forms. Example 1 shows one method for accomplishing this. A still further method would be to remove all the liquid medium in contact with the BPA-BI used in the process of making the latter and then washing the remaining crystalline material with, e.g., methanol, to remove the impurities.

The following example illustrates still another method (beginning with the making of the BPA-BI) for using the methanol or any of the other solvents employed in the practice of the present invention for obtaining purified BPA-BI by precipitating the purified BPA-BI.

EXAMPLE 2

A mixture of 14.8 grams of bisphenol-A, 9.95 grams of 50% aqueous sodium hydroxide, 62.5 ml dimethylsulfoxide and 62.5 ml toluene was heated at the reflux temperature of the mass under a nitrogen atmosphere. Water was removed azeotropically from the reaction mixture using a Dean-Stark trap. After all visible signs of water had been removed, a recirculating CaH$_2$ trap was employed to remove the last traces of water. At this time 21 ml toluene was removed from the system to give a 60:40 solvent ratio (dimethylsulfoxide:toluene). The solution was cooled to 60° C. and 26.92 grams of 4-nitro-N-methylphthalimide was added. The reaction mixture was stirred at 60° C. for 6 hours under a nitrogen atmosphere, and then cooled to room temperature and diluted with 250 ml of methylene chloride. The organic solution was extracted with 200 ml of water and then a number of times with 0.6N HCl until all traces of dimethylsulfoxide had been removed. The methylene chloride solution thus obtained was dried over magnesium sulfate and the methylene chloride was partly removed until only 100 ml of a homogeneous solution was left. This solution was then added to 1 liter of methanol in a blender and the resulting precipitate which formed was filtered and dried to give 30.81 grams (about a 91% yield) of the BPA-BI of the formula described in Example 1. The use of $^{13}C$ NMR established that the BPA-BI was essentially pure as further evidenced by its melting point of 145°-147° C.

The bisimide can be employed as a plasticizer for organic polymers such as polyvinyl chloride, polyimides, etc. When the bisimide is converted to the dianhydride of formula I, which in turn is reacted with an organic diamine, polyimides are obtained which because of their high temperature resistance can be used in applications where such properties are desired. Including uses to which such polyimides can be made are, for instance, as molded products and films employed in applications such as for automobile uses, as coatings for electrical conductors for insulation purposes, as gears, handles for cooking utensils, etc.

We claim:

1. The process for purifying a 4-isomer bisimide of the formula

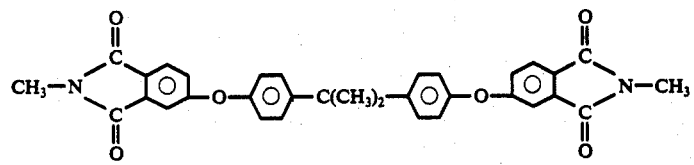

which contains as impurities, at least one of an imide compound selected from the class consisting of

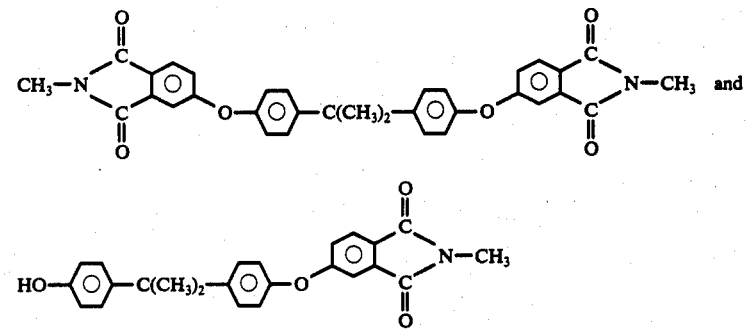

which process comprises dissolving at a temperature from 20° to 100° C. the aforementioned 4-isomer bisimide in methanol, for a period of time sufficient to take up in said solvent these impurities, and separating the purified 4-isomer bisimide substantially free of the impurities.

* * * * *

UNITED STATES PATENT AND TRADEMARK OFFICE
CERTIFICATE OF CORRECTION

PATENT NO. : 4,048,190
DATED : September 13, 1977
INVENTOR(S) : Donald S. Johnson and Frank J. Williams, III It is certified that error appears in the above-identified patent and that said Letters Patent are hereby corrected as shown below:

Column 4, line 12, change "1421-145" to - 142-145 -

In the single claim, change the second formula in the claim to read as follows

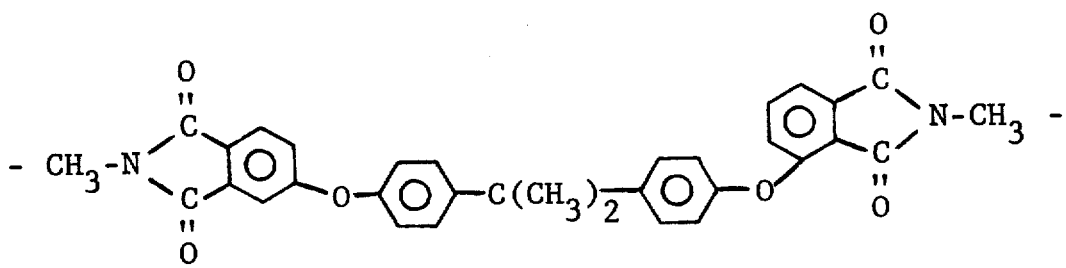

Signed and Sealed this

Twenty-first Day of February 1978

[SEAL]

Attest:

RUTH C. MASON
Attesting Officer

LUTRELLE F. PARKER
Acting Commissioner of Patents and Trademarks